United States Patent [19]

Roth et al.

[11] Patent Number: 4,587,341
[45] Date of Patent: May 6, 1986

[54] 2,4-DIAMINO-5-(1,2,3,4-TETRAHYDRO-(SUBSTITUTED OR UNSUBSTITUTED)-6-QUINOLYLMETHYL)-PYRIMIDINES, USEFUL AS ANTIMICROBIALS

[75] Inventors: Barbara Roth, Chapel Hill; Barbara S. Rauckman, Durham, both of N.C.

[73] Assignee: Burroughs Wellcome Co., Research Triangle Park, N.C.

[21] Appl. No.: 490,198

[22] Filed: Apr. 29, 1983

[30] Foreign Application Priority Data

May 7, 1982 [GB] United Kingdom ............... 8213249

[51] Int. Cl.⁴ .................. C07D 239/49; C07D 401/06; C07D 405/06; A61K 31/505
[52] U.S. Cl. .................................................... 544/324; 544/114; 544/295; 544/325; 546/141; 546/145; 546/153; 546/176
[58] Field of Search ............... 424/251; 544/325, 324; 514/275

[56] References Cited

U.S. PATENT DOCUMENTS 3,819,629  6/1974  Roth ..................... 544/325
4,039,543  8/1977  Kompis et al. ........... 544/325
4,438,267  3/1984  Daluge et al. ........... 544/325

FOREIGN PATENT DOCUMENTS 54756    6/1982  European Pat. Off. ........... 544/325
957797   5/1964  United Kingdom ............... 544/325
2087881  6/1982  United Kingdom ............... 424/251

Primary Examiner—Donald G. Daus
Assistant Examiner—Cecilia Shen
Attorney, Agent, or Firm—Donald Brown

[57] ABSTRACT

Compounds of the formula (II)

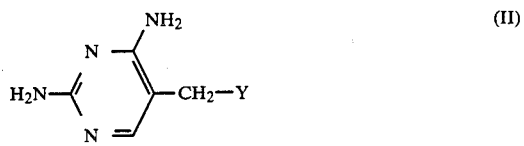

or a salt, N-oxide or acyl derivative thereof, wherein Y is a group

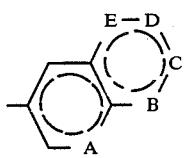

which is optionaly substituted and which optionally contain a nitrogen atom at one of positions A, B, C, D or E, in which the dotted line represents aromatic rings unless one of the rings contains a nitrogen atom in which case this ring is either aromatic or partially saturated, have antimicrobial properties. Processes for making these compounds, pharmaceutical compositions containing them and the medical use of the compounds are also disclosed.

3 Claims, No Drawings

2,4-DIAMINO-5-(1,2,3,4-TETRAHYDRO-(SUBSTITUTED OR UNSUBSTITUTED)-6-QUINOLYLMETHYL)-PYRIMIDINES, USEFUL AS ANTIMICROBIALS

The present invention relates to novel 2,4-diamino-5-(substituted) pyrimidines, to pharmaceutical compositions containing them, to processes for preparing them and their compositions, to intermediates for making them and to their use in the treatment of microbial infections.

Certain 2,4-diamino-5-benzylpyrimidines have been demonstrated to be potent inhibitors of dihydrofolate reductase (DHFR) which catalyses the reduction of dihydrofolic acid to tetrahydrofolic acid (THFA). This property has been shown frequently to result in useful pharmaceutical properties particularly in the treatment of bacterial infections. Thus, U.K. Patent Specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl)pyrimidine, is specifically disclosed in U.K. Pat. No. 875,562 and is the most active general antibacterial agent amongst the 2,4-diamino-5-benzylpyrimidines known to date. Due to their mode of action, these benzylpyrimidines potentiate the antibacterial activity of the sulphonamides and trimethoprim has been used extensively over the last decade in human therapy in combination with various sulphonamides, and in particular with sulphamethoxazole, for the treatment of bacterial infections.

European Patent Application No. 81109631.2 discloses compounds of the formula (I):

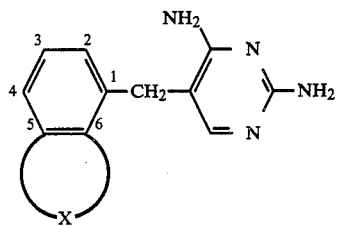

or a salt, N-oxide or acyl derivative thereof, wherein $\overline{X}$ is a six membered ring optionally containing a hetero atom, both the phenyl ring the $\overline{X}$ ring being optionally substituted except that when $\overline{X}$ does not contain a hetero atom either or both the phenyl ring or $\overline{X}$ must be substituted other than solely by a hydroxy group at the 4-position of the phenyl ring, and; that there are no substituents attached to the atom of $\overline{X}$ adjacent to the 6-position of the phenyl ring.

It has now been found that a further group of novel 2,4-diamino-5-(substituted)-pyrimidines has advantageous properties for the treatment of microbial infections. Accordingly, the present invention provides a compound of the formula (II):

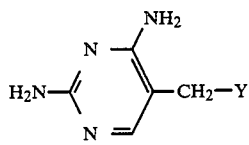

or a salt, acyl derivative or N-oxide thereof wherein Y is a group

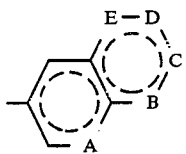

optionally containing a nitrogen atom at one of positions A, B, C, D or E, in which the dotted line represents aromatic rings unless one of the rings contains a nitrogen atom in which case this ring is either aromatic or partially saturated.

Either one or both of the rings may be substituted. Suitable substituents include halogen atoms, alkenyl, alkenyloxy, nitro, cyano, mercapto, alkylthio, substituted sulphoxyloxy, substituted sulphonyl, substituted sulphinyl, substituted carbonyl, substituted alkyl or optionally substituted alkoxy groups. Suitably Y contains from one to three substituents which substitute the A, B, C, D or E positions. Preferred substituents include methoxy, ethoxy, methoxyethoxy, methyl, ethyl, propyl, amino and dimethylamine groups.

When one of the rings contains a nitrogen atom and the dotted line represents a partially saturated ring, then substitution may occur on the nitrogen atom as well as on the carbon atoms contained within the rings. Particularly suitable substituents for this nitrogen atom include optionally substituted alkyl, alkenyl, nitroso and optionally substituted amino groups. Preferred substituents for the nitrogen atom include methyl and ethyl groups.

Suitable substituents for the alkyl and alkoxy groups include halogen atoms or hydroxy, phenoxy or $C_{1-2}$ alkoxy groups. Suitable substituents for amino groups include $C_{1-4}$ alkyl or $C_{1-4}$ acyl groups or the nitrogen atom forming part of a five or six membered heterocyclic ring. Suitable substituents for the sulphonyloxy, sulphonyl and sulphinyl groups include $C_{1-4}$ alkyl, optionally substituted by phenyl, and phenyl groups. Suitable substituents for the carbonyl and carboxyl groups include $C_{1-4}$ alkyl groups.

A preferred group of compounds of the formula (II) is that wherein Y is a group

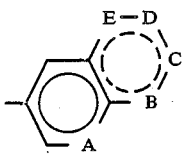

wherein one of B, C, D and E is a nitrogen atom and the others and A are carbon atoms and the dotted line represents an aromatic ring or a partially saturated ring. Suitably, there are one to three substituents at the A, B, C, D or E positions.

When C or D are nitrogen atoms, the dotted line is suitably an aromatic ring.

When E is a nitrogen atom, the dotted line is suitably a saturated ring.

When B is a nitrogen atom, the dotted line is suitably either and aromatic ring or a saturated ring.

When the dotted line is an aromatic ring, preferred substituents include optionally substituted $C_{1-4}$ alkyl, optionally substituted C$_{1-4}$ alkoxy, optionally substituted amino, C$_{1-4}$ alkythio, C$_{2-4}$ alkenyl or C$_{2-4}$ alkenyloxy. Particularly preferred substituents include methoxy, ethoxy, methyl, ethyl, amino, dimethylamino or pyrrolyl.

When the dotted line represents a partially saturated ring the nitrogen atom is suitably optionally substituted by C$_{1-4}$ alkyl, optionally substituted by halogen, hydroxy or C$_{1-2}$ alkoxy, formyl, a group C(O)$_n$R$^1$R$^2$ wherein n is the integer 1 or 2 and R$^1$ and R$^2$ are the same or different and each is a C$_{1-4}$ alkyl, nitro or a NR$^3$R$^4$ group wherein R$^3$ and R$^4$ are the same or different and each is hydrogen or C$_{1-4}$ alkyl or NR$^3$R$^4$ is a five or six membered heterocyclic ring, and one or more or the other positions A, B, C, D and E are suitably substituted by C$_{1-4}$ alkyl or C$_{1-4}$ alkoxy each optionally substituted by halogen atoms, hydroxy or C$_{1-2}$ alkoxy groups or by C$_{2-4}$ alkenyl groups.

Suitably B is a nitrogen atom. A further preferred group of compounds of the formula (II) is that wherein Y is a group

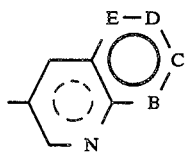

wherein B, C, D and E are carbon atoms and the dotted line represents an aromatic ring or a partially saturated ring. Suitably, there are one to three substituents at the B, C, D and E positions. B, C, D or E are optionally substituted by C$_{1-4}$ alkyl or C$_{1-4}$ alkoxy groups each optionally substituted by halogen, hydroxy or C$_{1-2}$ alkoxy, halogen, C$_{1-4}$ alkylthio, a group C(O)$_n$R$^1$R$^2$ a group NR$^3$R$^4$ or a group CONR$^1$R$^2$ or SO$_2$NR$^1$R$^2$ wherein R$^1$, R$^2$, R$^3$ and R$^4$ are as hereinbefore defined.

A further preferred group of compounds of the formula (II) is that wherein Y is a group:

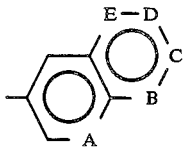

wherein A, B, C, D and E are carbon atoms. Suitably, there are substituents attached at one to three A, B, C, D and E. Particularly suitable substituents include C$_{1-4}$ alkyl or C$_{1-4}$ alkoxy each optionally substituted by halogen, hydroxy, or C$_{1-2}$ alkoxy, halogen, C$_{1-4}$ alkyl or C$_{2-4}$ alkenyl.

Particularly preferred compounds of the present invention include:
2,4-diamino-5-(1,2,3,4-tetrahydro-6-quinolylmethyl)-pyrimidine dihydrochloride,
2,4-diamino-5-(1,2,3,4-tetrahydro-8-methoxy-6-quinolylmethyl)pyrimidine
2,4-diamino-5-(1,2,3,4-tetrahydro-8-(2-methoxyethoxy)-6-quinolylmethyl)pyrimidine,
2,4-diamino-5-(1,2,3,4-tetrahydro-4-methyl-6-quinolylmethyl)-pyrimidine dihydrochloride,
2,4-diamino-5-(2-naphthylmethyl)pyrimidine, and
2,4-diamino-5-(3-quinolylmethyl)pyrimidine.

The compounds of the formula (II) are bases and, as such, form acid addition salts with acids. Suitable acid addition salts of the compounds of the formula include those formed with both organic and inorganic acids. Such acid addition salts will normally be pharmaceutically acceptable. Thus, preferred salts include those formed from hydrochloric, sulphuric, citric, tartaric, phosphoric, lactic, benzoic, glutamic, aspartic, pyruvic, acetic, succinic, fumaric, maleic, oxaloacetic, isethionic, stearic, fumaric, methanesulphonic, p-toluenesulphonic, lactobionic and glucuronic acids.

Suitable acyl derivatives are those wherein an amino group is substituted by a group —COM wherein M is hydrogen or C$_{1-11}$ alkyl or C$_{2-11}$ alkenyl, preferably C$_{1-4}$ alkyl or C$_{2-4}$ alkenyl, optionally substituted by carboxy, carb-C$_{1-4}$ alkoxy, nitrile, amino, chlorine or phenoxy optionally substituted by halogen, methyl or methoxy, the alkyl or alkenyl groups being optionally interspersed with one or more oxygen atoms or forming part or the whole of a cycloaliphatic ring or may represent a C$_{6-10}$ aromatic or C$_{6-10}$ araliphatic residue optionally substituted by one or more chlorine atoms or methyl, OCH$_2$COOH, carb-C$_{1-4}$ alkoxy or a heterocyclic group containing one or more nitrogen, oxygen or sulphur atoms.

Preferred acyl derivatives are those wherein the amino group at the 2-position of the pyrimidine ring is substituted, particularly those wherein the amino group is substituted by acetyl or by an acyl group derived from an amino such as a glycyl group.

Suitable N-oxides of compounds of the formula (II) include those formed by oxidation of either or both of the nitrogen atoms in the pyrimidine ring or by oxidation of the nitrogen in the bicyclic ring system when this is present.

The preparation of salts, acyl derivatives and N-oxides is carried out by conventional methods well known to those skilled in the art.

Pharmaceutically acceptable acid addition salts of compounds of the formula (II) form a particularly preferred aspect of the present invention.

In a further aspect, the present invention provides a pharmaceutical composition comprising a compound of the formula (II) in combination with a pharmaceutically acceptable carrier. By the terms "pharmaceutical composition" and "pharmaceutically acceptable carrier" are meant those compositions and carriers suitable for use in human and/or veterinary medicine.

The compounds of the formula (II) can conveniently be presented in the compositions of the present invention in an effective unit dosage form, that is to say in an amount sufficient to be effective against the bacterial organism in vivo.

The pharmaceutically acceptable carriers present in the compositions of the present invention are materials recommended for the purpose of administering the medicament. These may be liquid, solid or gaseous materials, which are otherwise inert or medically acceptable and are compatible with the active ingredient.

These pharmaceutical compositions may be given parenterally, orally, used as a suppository, applied as an ophthalmic solution, or applied topically as an ointment, cream or powder. However, oral and parenteral administration of the compositions is preferred for human use. For veterinary use, intramammary as well as oral and parenteral administration is preferred.

For oral administration, fine powders or granules will contain diluting, dispersing and/or surface active agents, and may be presented in a draught, in water or in a syrup, in capsules or cachets in the dry state or in a non-aqueous suspension wherein suspending agents may be included, or in a suspension in water or syrup. Where desirable or necessary, flavouring, preserving, suspending, thickening or emulsifying agents can be included.

For parenteral administration, the compounds may be presented in sterile aqueous injection solutions which may contain antioxidants or buffers.

As stated above, free base or a salt thereof may be administered in its pure form unassociated with other additives in which case a capsule or cachet is the preferred carrier.

Other compounds which may be included are, for example, medically inert ingredients, e.g. solid and liquid diluents such as lactose, glucose, starch or calcium phosphate for tablets or capsules; olive oil or ethyl oleate for soft capsules; and water or vegetable oil for suspensions or emulsions; lubricating agents such as talc or magnesium stearate; gelling agents such as colloidal clays; thickening agents such as gum tragacanth or sodium alginate; and other therapeutically acceptable accessory ingredients such as humectants, preservatives, buffers, and antioxidants which are useful as carriers in such formulations.

Alternatively the active compound may be presented in a pure form as an effective unit dosage, for instance, compressed as a tablet or the like.

For veterinary use, different intramammary formulations will normally be prepared for use in dry cows and for use in milking cows. Thus, formulations for dry cow use will normally be in an oil, such as peanut oil, gelled with a gelling agent such as aluminium monostearate. Formulations for milking cow use will usually contain an emulsifying agent (for example Tween 20 or a polysorbate) and a milk miscible carrier such as peanut oil or a mineral oil.

It may be advantageous to include the compounds of formula (II) in a pharmaceutical composition which includes other active ingredients for example p-aminobenzoic acid competitors such as sulphonamides.

Of known p-aminobenzoic acid competitors, the following sulphonamide compounds (or pharmaceutically acceptable salts thereof) are particularly useful:

Sulfanilamide, Sulfadiazine, Sulfamethisazole, Sulfapyridine, Sulfathiazole, Sulfamerazine, Sulfamethazine, Sulfisoxazole, Sulformethoxine, 2-(p-Aminobenzenesulfonamide-3-methoxypyrazine (Kelfizina), Mafenide, 5-Sulfanilamido-2,4-dimethyl-pyrimidine, 4-($N^1$-Acetylsulfanilamido)-5,6-dimethoxypyrimidine, 3-Sulfanilamido-4,5-dimethylisoxazole, 4-Sulfanilamido-5-methoxy-6-decyloxypyrimidine sulfamono-methoxine, 4-p-(8-Hydroxyquinolinyl-4-azo)-phenylsulfanilamido-5,6-dimethoxy-pyrimidine, Sulfadimethoxine, Sulfadimidine, Sulfamethaxazole, Sulfamoxole, Sulfadoxine, Sulfaguanidine, Sulfathiodimethoxine, Sulfaquinoxaline, and p-(2-Methyl-8-hydroxyquinolinyl-5-azo)-phenylsulfanilamido-5,6-dimethoxy-pyrimidine.

However, the most preferred combinations include those containing Sulfadiazine, Sulfamethoxazole, Sulfadoxine, Sulfamoxole or Sulfadimidine. The ratio of the compound of the formula (II) to sulphonamide will normally be from 3:1 to 1:10, for example 1:1 to 1:5. A particularly preferred composition of the present invention comprises a compound of formula (II) and a sulphonamide in a ratio of 1:2 to 1:5 preferably together with a pharmaceutically acceptable carrier.

Tablets or other forms of presentation provided in discrete units may conveniently contain an amount of compound of the formula (II) which is effective at a dosage or as a multiple of the same, for instance for human use, units containing 2.5 to 200 mg usually around 30 to 100 mg and for veterinary use, units containing 30 to 500 mg.

The pharmaceutical compositions of the present invention can be prepared by the admixture of a compound of the formula (II) with a pharmaceutically acceptable carrier. Other active ingredients, such as a sulfonamide, or conventional pharmaceutical excipients may be admixed as required.

The compounds of the present invention are useful for the treatment of microbial infections and, in particular, gram negative aerobic, gram positive aerobic or anaerobic bacterial infections in mammals. They are particularly useful in the treatment of Staphylococcal infections for example mastitis in cattle, Neisseria infections in humans, for example *N. gonorrhea*, acne in humans, and anaerobic infections. Most compounds also have an excellent level of general antibacterial activity.

Still another aspect of the present invention provides a method for the treatment or prophylaxis of bacterial infections in mammals by the administration of an effective non-toxic antibacterial amount of a compound of formula (II) or a pharmaceutically acceptable salt thereof, or a composition as hereinbefore described.

As indicated above, the compounds of the formula (II) are generally useful in treating bacterial infections by rectal, parenteral, topical or oral administration. The compounds of formula (II) are normally administered at a dose from 0.1 mg/kg to 30 mg/kg per day and preferably 1 mg/kg to 10 mg/kg. The dose range for adult humans is generally from 25 to 300 mg/day and preferably 100 to 200 mg/day.

The dose range for intramammary administration of the compounds of the formula (II) is generally from 100 to 500 mg, preferably 200 mg to 400 mg, per quarter of the udder to dry cows. Milking cows will normally receive four to six medications of a composition of the present invention, a dose being conveniently administered at milking time (i.e. twice daily) to each of the desired quarters of the udder. Dry cows will normally receive only one medication of a composition of the present invention, one dose being provided to each of the four quarters of the udder.

The compounds of formula (II) and their pharmaceutically acceptable salts may be prepared by methods known for the synthesis of compounds of analogous structure.

Thus the present invention provides a process for preparation of compounds of the formula (II) as hereinbefore defined which process comprises:

(a) (i) the reaction of a guanidine salt with a compound of the formula (V) or (VI):

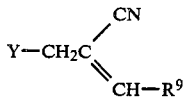

(VI)

wherein Y is as hereinbefore defined and is optionally substituted as hereinbefore defined, $R^8$ is a $C_{1-4}$ alkyl group and $R^9$ is a nucleophilic leaving group such as a $C_{1-4}$ alkoxy group, for example, a methoxy, ethoxy or methoxyethoxy group, or an amino, $C_{1-4}$ alkylamino, benzylamino, di-($C_{1-4}$)alkylamino, naphthylamino, optionally substituted anilino, morpholino, piperidino or N-methyl piperazino group and most preferably $R^9$ is an anilino group:

(ii) the reaction of a compound of the formula (VII):

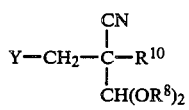

(VII)

wherein Y and $R^8$ are as hereinbefore defined and is optionally substituted as hereinbefore defined and $R^{10}$ is an alkoxycarbonyl or aldehyde group, with potassium or sodium hydroxide in a $C_{1-4}$ alkanol followed by addition of guanidine;

(b) (i) the reaction of a compound of the formula (VIII):

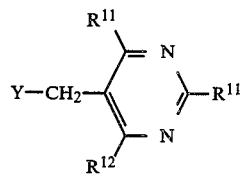

(VIII)

wherein $R^{11}$ is an amino group or a leaving group, such as a $C_{1-4}$ alkylthio group or a halogen atom, $R^{12}$ is a hydrogen or halogen atom, except that both groups $R^{11}$ cannot be amino groups and Y contains a partially saturated ring as hereinbefore defined and is optionally substituted as hereinbefore defined with an aminating agent such as ammonia and thereafter when $R^{12}$ is a halogen atom removing this by hydrogenolysis;

(ii) the reaction of a compound of the formula (IX):

Y—CH$_2$Z    (IX)

wherein Z is a halogen atom, hydroxy, di-$C_{1-4}$ alkyl substituted amino or other leaving group and Y is as hereinbefore defined and is optionally substituted as hereinbefore defined with a compound of the formula (X):

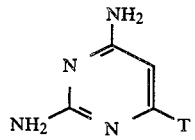

(X)

wherein T is a hydrogen, hydroxy or $C_{1-4}$ alkylthio group, and then when T is not hydrogen coverting the group T to hydrogen by hydrogenolysis when T is a $C_{1-4}$ alkylthio group or, when T is a hydroxy group, by first converting it to the mesylate or tosylate derivative or to thio, alkylthio or halogen and then removing this by hydrogenolysis;

(c) the conversion of one compound of the formula (II) to a different compound of the formula (II) for example by the reduction of the double bonds, formation of a quinoline from the corresponding tetrahydroquinoline, conversion of a hydroxy group to $C_{1-4}$ alkylthio group or an optionally substituted $C_{1-4}$ alkoxy group or conversion of an amino group to a $C_{1-4}$ alkylthio group or hydrogen, halogen, hydroxy or cyano via a diazo group or to a substituted amino group by methods well known to those skilled in the art.

The reaction of guanidine with a compound of the formula (V) or (VI) will take place under conditions analogous to those described in U.K. Pat. Nos. 1 133 766 and 1 261 455 respectively for the preparation of structurally related benzylpyrimidines. Conveniently the reaction is carried out in a $C_{1-4}$ alkanol, for example methanol or ethanol. The compounds of the formula (V) and (VI) may be prepared by methods known in the art.

The reaction of a compound of the formula (VII) with guanidine and the preparation of the compounds of the formula (VII) will be carried out by methods analogous to those described in Belgian Pat. No. 855 505.

In the compounds of the formula (II) when $R^{11}$ or $R^{12}$ are halogen atoms these are suitably chlorine or bromine atoms. The reaction may conveniently be carried out under the reaction conditions described in U.K. Pat. Nos. 875 562 and 1 132 082. The reduction of $R^{12}$ when this is halogen will suitably be carried out under the conditions described in German Offenlegungschrift No. 2258238. This is not a preferred method for preparing those compounds wherein $R^3$ or $R^4$ are groups that are susceptible to catalytic hydrogenation.

The compounds of formula (II) may be prepared by methods known in the art, for example as described in U.K. Pat. Nos. 875562 and 1132082 or German Offenlegungschrift No. 2258238. The compounds of the formula (II) wherein $R^{11}$ and/or $R^{12}$ are halogen atoms may conveniently be prepared from the corresponding compounds wherein $R^{11}$ and/or $R^{12}$ are hydroxy. These compounds may be prepared by methods analogous to these described in the art or by the reaction of a compound of the formula (YH) with 5-dimethylaminomethyluracil or 5-hydroxymethyluracil. This reaction will normally be carried out in an inert high boiling polar solvent, for example a high boiling $C_{2-6}$ alkanol such as ethylene glycol, at between 100° and 200° C. for example between 130° and 160° C. The reaction will normally be carried out under basic conditions when the phenyl ring is substituted by hydroxy, for example in the presence of sodium methoxide, and under neutral conditions when the phenyl ring is substituted by amino or substituted amino.

Certain compounds of the formula (VIII) wherein the phenyl ring is substituted by a hydroxy group may be converted to compounds of the formula (VIII) wherein the phenyl ring is substituted by an alkoxy or thio $C_{1-4}$ alkyl group and certain compounds of the formula (VIII) wherein the phenyl ring is substituted by an amino group and $R^{11}$ is a hydroxyl group may be converted to compounds of the formula (VIII) wherein the phenyl ring is substituted by $C_{1-4}$ alkylthio, halogen, cyano, substituted amino group or hydrogen by methods well known to those skilled in the art.

Suitably Z is a dialkylamino or cyclic amino group containing up to 10 carbon atoms; a dimethylamino group is particularly convenient. The reaction will be carried out under conditions well known to those skilled in the art of Mannich reactions. It has been found that the reaction may suitably be carried out at an elevated temperature, suitably between 100° and 200° C. in a solvent having a suitably high boiling point, for example a glycol such as ethylene glycol. The dethiation is suitably carried out by hydrogenolysis in the presence of a transition metal catalyst; Raney nickel is particularly suitable for this purpose. This reaction will normally be carried out in a polar solvent, for example $C_{1-4}$ alkanol such as methanol or ethanol.

Again, this is not a preferred method of preparing those compounds of the formula (II) wherein there are groups that are susceptible to a catalytic hydrogenation.

The compounds of the formula (XI) wherein X is sulphur or oxygen may be prepared by reaction schemes A and B respectively:

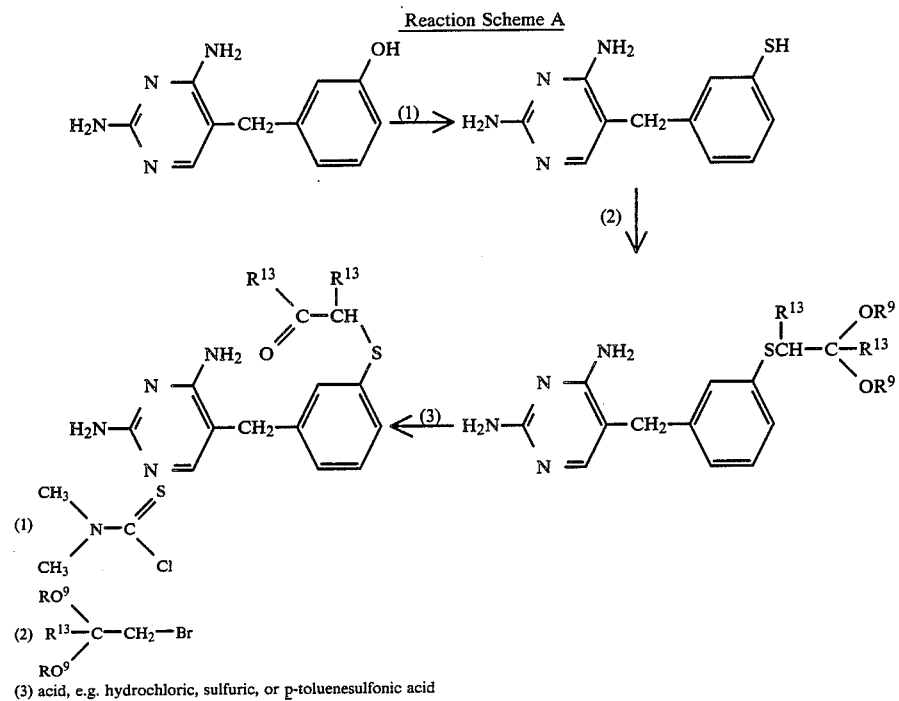

The compounds of the formula (XII) wherein X is other than oxygen or sulphur will be made by methods analogous to those described in the art.

The cyclisation of a compound of the formula (XI) will take place under conventional conditions, for example those described in "The Chemistry of Heterocyclic Compounds," Wiley-Interscience, John Wiley & Sons, Inc., N.Y.: *The Indoles, Part One*, vol. 25, p. 317 ff (1972); "Heterocyclic Compounds," vol. 2, R. C. Elderfield, ed., John Wiley & Sons, Inc., N.Y., p. 11 ff, p. 146 ff (1951); "Advances in Heterocyclic Chemistry," vol. 11, A. R. Katritzky and A. J. Boulton, ed., Academic Press, N.Y., p. 217 ff (1970); and "Advances in Heterocyclic Chemistry," vol. 18, A. R. Katritzky and A. J. Boulton, ed., Academic Press, N.Y., p. 362 ff (1975).

The preparation of a compound of the formula (XI) from the corresponding acetal and its conversion to the corresponding compound of formula (II) will conveniently take place in situ.

It is preferred that the phenyl ring be suitably substituted in order that cyclisation proceeds at the 2-position.

The reaction of a compound of the formula (XII) with 2,4-diamino-5-hydroxymethylpyrimidine will normally be carried out under the reaction conditions described in U.K. Pat. No. 1413471. Thus the reaction will conveniently be carried out in a polar non-phenolic solvent capable of dissolving both reactants at a non-extreme temperature, for example between 50° C. and 150° C. The reaction is preferably carried out in the presence of a strong acid catalyst, such as hydrochloric, acetic, methanesulphonic or p-toluenesulphonic acids.

In the case where there is an alkoxy group at the 4-position, it may be necessary to separate the desired compound of the formula (III) from other substances present in the reaction mixture.

It will be apparent to those skilled in the art that when certain ring substituents are present in the final compounds of the formula (II) certain methods of preparation will preferably not be used to make these compounds due to the possibility of the reaction conditions changing the final product group, for example hydrogenolysis or addition across the double bond when a double bond is present.

Certain compounds of the formula (II) whilst having some antibacterial activity in their own right are also useful as intermediates in the preparation of other compounds of the formula (II) having interesting antibacterial activity.

The intermediates of the formula (V) to (IX), and (XI) which are novel form a further aspect of the present invention.

In yet another aspect, the present invention provides the first use of the compounds of the formula (II) in human and veterinary medicine. The preferred human use of the compounds of the formula (II) is in the treatment or prophylaxis of *bacterial* infections.

The following examples illustrate the preparation of the compounds of the present invention and their pharmacological properties. All temperatures are in degress centigrade.

EXAMPLE 1

2,4-Diamino-5-(1,2,3,4-tetrahydro-6-quinolylmethyl)-pyrimidine Dihydrochloride

A mixture of 1,2,3,4-tetrahydroquinoline (2.66 g, 0.02 mol), 2,4-diamino-5-hydroxymethylpyrimidine (2.80 g, 0.02 mol), glacial acetic acid (35 ml) and concentrated hydrochloric acid (3.45 ml) was heated under reflux for 3.5 hours. The solution was filtered from a small precipitate, and the solvent was removed. The residue was dissolved in water and made basic with ammonium hydroxide, which resulted in the precipitation of a gummy solid. This was extracted into 3:1 methylene chloride:methanol several times. The extract was evaporated leaving a residue (3.45 g) which was dissolved in a mixture of 9:1 methylene chloride:methanol and put through a short silica gel column. There was isolated 2,4-diamino-5-(1,2,3,4-tetrahydro-6-quinolylmethyl)-pyrimidine (2.85 g), which was converted to the dihydrochloride with ethanol-HCl, m.p. 284°–287° C. Anal. Calcd. for $C_{14}H_{17}N_5.2HCl$: C, 51.23; H, 5.83; N, 21.34; Cl, 21.60. Found: C, 51.22; H, 5.86; N, 21.32; Cl, 21.54.

EXAMPLE 2

2,4-Diamino-5-(1,2,3,4-tetrahydro-8-methoxy-6-quinolylmethyl)pyrimidine

8-Methoxy-1,2,3,4-tetrahydroquinoline (J. L. Neumeyer and J. G. Cannon, J. Pharm. Sci., 51, 804 (1962)) (2.88 g) was treated by the method of Example 1 with 2,4-diamino-5-hydroxymethylpyrimidine. The product crystallized from the reaction mixture as an off-white solid, which was washed with water and treated with ammonia, followed by recrystallization from absolute ethanol (5.0 g). A slight impurity was removed on a silica gel column, which was eluted with 19:1 methylene chloride:methanol, taken to dryness, and recrystallized once more from absolute ethanol; m.p., 201°–203° C. Anal. Calcd. for $C_{15}H_{19}N_5O$: C, 63.14; H, 6.71; N, 24.54. Found: C, 63.23; H, 6.75; N, 24.47.

EXAMPLE 3

2,4-Diamino-5-(1,2,3,4-tetrahydro-8-(2-methoxyethoxy)-6-quinolylmethyl)pyrimidine A. 8-Methoxyethoxyquinoline To 8-hydroxyquinoline (9.47 g, 0.065 mol) in dimethyl sulfoxide (50 ml) was added 2-methoxyethyl bromide (8.96 g, 0.065 mol). The mixture was stirred at room temperature for two hours, and turned a dark red. The solvent was removed under vacuum, and the residue dissolved in water. The aqueous solution was extracted several times with ethyl acetate, and the ethyl acetate solution was then washed well with water, dried, and the solvent removed; the residual oil weighed 7.45 g. This was purified on a silica gel column, eluted with heptane:ethyl acetate, with increasing proportions of the latter. There was isolated 8-methoxyethoxyquinoline (7.11 g) as a light blue oil. NMR: ($CDCl_3$) δ 3.51 (s, 3, OMe), 4.01 (tr, 2, $CH_2$), 4.48 (tr, 2, $CH_2$), 7.20 (m, 1, beta-pyridine-H), 7.45 (m, 3, Ar), 8.15 (dd, 1, gamma-pyridine-H), 8.98 (dd, 1, alpha-pyridine-H). Anal. Calcd. for $C_{12}H_{13}NO_2$: C, 70.92; H, 6.45; N, 6.89. Found: C, 70.80; H, 6.49; N, 6.90.

B. 1,2,3,4-Tetrahydro-8-methoxyethoxyquinoline

8-Methoxyethoxyquinoline (6.48 g, 31.9 mmol) was dissolved in methanol (50 ml) and reduced on a Parr hydrogenation apparatus using $PtO_2$ catalyst. The catalyst was removed, and the solution was taken to dryness. The dark brown oil which remained was purified on a short silica gel column using 4:1 heptane:ethyl acetate for elution. The isolated oil (1,2,3,4-tetrahydro-8-methoxyethoxyquinoline) had the following NMR spectrum: ($CDCl_3$) δ 1.93 (quintet, 2, $CH_2$ (beta-H)), 2.76 (tr, 2, $CH_2$), 3.32 (tr, 2, $CH_2$), 3.43 (s, 3, OMe), 3.72 (tr, 2, $OCH_2$), 4.11 (tr, 2, $CH_2O$), 4.31 (br, 1, NH), 6.57 (s, +sh, 3, Ar-3H). Anal. Calcd. for $C_{12}H_{17}NO_2$: C, 69.54; H, 8.27; N, 6.76. Found: C, 69.42; H, 8.26; N, 6.70.

C. 2,4-Diamino-5-(1,2,3,4-tetrahydro-8-(2-methoxyethoxy)-6-quinolylmethyl)pyrimidine The procedure of Example 1 was used to react 1,2,3,4-tetrahydro-8-methoxyethoxyquinoline (3.11 g)

with 2,4-diamino-5-hydroxymethylpyrimidine, and 2,4-diamino-5-(1,2,3,4-tetrahydro-8-(2-methoxyethoxy)-6-quinolylmethyl)pyrimidine was isolated and purified as in this example. The free base was recrystallized from absolute ethanol; m.p. 149°–151° C. NMR (Me$_2$SO-d$_6$) δ 1.76 (m, 2, CH$_2$), 2.61 (tr, 2, CH$_2$), 3.22 (m, 2, CH$_2$), 3.31 (s, 3, OMe), 3.39 (s, 2, bridge CH$_2$), 3.65 (m, 2, CH$_2$CH$_2$O), 3.97 (m, 2, OCH$_2$CH$_2$), 4.60 (br. s., 1, NH), 5.60 and 5.90 (2 br s, 4, (NH$_2$)$_2$), 6.36 (d, 1, J=1–2, Ar), 6.53 (d, 1, J=1–2, Ar), 7.45 (s, 1, pyrimidine-6-H). Anal. Calcd. for C$_{17}$H$_{23}$N$_5$O$_2$: C, 61.99; H, 7.04; N, 21.26. Found: C, 61.82; H, 7.06; N, 21.25.

EXAMPLE 4

2,4-Diamino-5-(1,2,3,4-tetrahydro-4-methyl-6-quinolylmethyl)pyrimidine Dihydrochloride A. 4-Methyl-1,2,3,4-tetrahydroquinoline A solution of lepidine (7.16 g) in methanol (50 ml) was reduced in a Parr hydrogenation apparatus with a total of 1.25 g of PtO$_2$ catalyst, added in 3 portions, at intervals. The reduction was very slow. After 36 hours, the catalyst was removed, and then the solvent was removed; the residual oil proved to be a mixture which still contained considerable lepidine. This was separated on a silica gel column using 10:1 hexane:ethyl acetate for elution. A 0.91 g portion was isolated which was 4-methyl-1,2,3,4-tetrahydroquinoline. NMR: (CDCl$_3$) δ 1.26 (d, 3, CHMe), 1.5–2.2 (m, 2, CH$_2$), 2.89 (septet, 1, CHMe), 3.26 (tr, 2, NCH$_2$), 3.78 (br s, 1, NH), 6.37–7.2 (m, 4, ArH$_4$). MS: 147 (M+). Anal. Calcd. for C$_{10}$H$_{13}$N: C, 81.58; H, 8.90; N, 9.51. Found: C, 81.54; H, 8.93; N, 9.47.

B. 2,4-Diamino-5-(1,2,3,4-tetrahydro-4-methyl-6-quinolylmethyl)pyrimidine Dihydrochloride 4-Methyl-1,2,3,4-tetrahydroquinoline (0.74 g, 0.005 mole) was treated with 2,4-diamino-5-hydroxymethyl-pyridimine in the manner of Example 1, and purified similarly, followed by conversion to the dihydrochloride salt in absolute ethanol-HCl. The dihydrochloride (0.54 g) melted at 280°–282° C. NMR: (Me$_2$SO-d$_6$) δ 1.26 (d, 3, CHMe, J=7 Hz), 1.70 (m, 2, CH$_2$), 2.90 (m, 1, CHMe), 3.30 (tr, 2, NCH$_2$), 3.69 (s, 2, bridge CH$_2$), ca. 4.0 (v br, 2, NH$_2^+$), 7.13 (s, 2, Ar), 7.33 (s, 1, Ar, J=1–2), 7.54 (s, 1, pyrimidine-6-H), 7.61 (br s, 2, NH$_2$), 7.77 and 8.25 (2 br s, 2, NH, NH), ca 12.0 (v br NH$^+$), Anal. Calcd. for C$_{15}$H$_{19}$N$_5$.2HCl: C, 52.64; H, 6.18; N, 20.46; Cl, 20.72. Found: C, 52.52; H, 6.24; N, 20.36; Cl, 20.60.

EXAMPLE 5

2,4-Diamino-5-(2-naphthylmethyl)pyrimidine

A. 2-(2-Naphthylmethyl)-3-anilinoacrylonitrile

To a mixture of 2-naphthaldehyde (4.69 g, 30 mmol) and beta-anilinopropionitrile (4.82 g, 33 mmol) in dimethyl sulfoxide (35 ml) was added potassium t-butoxide (3.70 g, 33 mmol). The solution immediately turned a dark red. It was heated at 100° for 30 minutes, cooled, and diluted with methanol (15 ml) and water (25 ml). A copious yellow precipitate formed, which was chilled and isolated. The precipitate, 2-(2-naphthylmethyl)-3-anilinoacrylonitrile, was washed with dilute methanol and hexane; yield, 7.65 g. A portion was recrystallized from absolute ethanol; m.p. 148°–153° C. Anal. Calcd. for C$_{20}$H$_{16}$H$_2$: C, 84.48; H, 5.67; N, 9.85. Found: 84.38; H, 5.69; N, 9.82.

B. 2,4-Diamino-5-(2-naphthylmethyl)pyrimidine 2-(2-Naphthylmethyl)-3-anilinoacrylonitrile (6.65 g, 23.4 mmol) was dissolved in absolute ethanol (225 ml) and heated to reflux. A solution of sodium methylate (4.27 g, 79 mmol) in ethanol (75 ml) was mixed with guanidine hydrochloride (6.87 g, 72 mmol), filtered from salt, and added to the solution of 2-(2-naphthylmethyl)-3-anilinoacrylonitrile. The mixture was then refluxed for 8 hours, and allowed to stand at room temperature overnight. A yellow precipitate formed, which was isolated (2.66 g). An additional 1.33 g was obtained by concentration of the mother liquor. The combined fractions were recrystallized from absolute ethanol, yielding light cream colored 2,4-diamino-5-(2-naphthyl-methyl)pyrimidine (3.0 g), m.p. 231°–233° C. Anal. Calcd. for C$_{15}$H$_{14}$N$_4$: C, 71.98; H, 5.64; N, 22.38. Found: C, 71.93; H, 5.68; N, 22.35.

EXAMPLE 6

2,4-Diamino-5-(3-quinolylmethyl)pyrimidine

A. 2-(3-Quinolylmethyl)-3-anilinoacrylonitrile

A mixture of 3-quinolinecarboxaldehyde (5.0 g, 31.8 mmol) and anilinopropionitrile (5.12 g, 35 mmol) was treated in the manner of Example 5 A to give 7.38 g (81%) of 2-(3-quinolylmethyl)-3-anilinoacrylonitrile. A sample was recrystallized from methyl cellosolve; m.p. 202°–203°. Anal. Calcd. for C$_{19}$H$_{15}$N$_3$: C, 79.98; H, 5.30; N, 14.73. Found: C, 79.80; H, 5.24; N, 14.73.

B. 2,4-Diamino-5-(3-quinolylmethyl)pyrimidine 2-(3-Quinolylmethyl)-3-anilinoacrylonitrile (6.38 g) was treated with guanidine in the manner of Example 5B. There was isolated 4.90 g (87%) of 2,4-diamino-5-(3-quinolylmethyl)pyrimidine which was recrystallized from methyl cellosolve with the aid of decolorizing charcoal; m.p. 279°–282° C. (dec). Anal. Calcd. for C$_{14}$H$_{13}$N$_5$: C, 66.92; H, 5.21; N, 27.87. Found: C, 66.57; H, 5.36; N, 27.54.

EXAMPLE 7

2,4-Diamino-5-(1,2,3,4-tetrahydro-8-methoxy-4-methyl-6-quinolylmethyl)pyrimidine A. 2-Chloro-8-methoxy-4-methylquinoline 8-Methoxy-4-methyl-2-quinoline (R. M. Forbis and K. L. Rinehart, Jr., *J. Am. Chem. Soc.*, 95, 5003 (1973)), 3.93 g., was treated with 6 ml. of phosphorus oxychloride at 120° for 2 hours, neutralised with 15 ml of concentrated ammonium hydroxide in 100 ml of ice to pH 9, and extracted with 2 times 100 ml of ethyl acetate; 4.24 g of product was obtained, which was purified on a silica gel column, eluted with heptane:ethyl acetate 3:1, to give 4.2 g. (97%) of 2-chloro-8-methoxy-4-methylquinoline (A), m.p. 106°–108°. NMR (CDCl$_3$) δ 2.66 (s, 3, Me), 4.05 (s, 3, OMe), 7.02 (m, 4, ArH$_3$, pyr-beta-H). Anal. Calcd. for C$_{11}$H$_{10}$CiNO: C, 63.62; H, 4.85; N, 6.75. Found: C, 63.59; H, 4.89; N, 6.72.

B. 8-Methoxy-4-methylquinoline

The product of A, 1.85 g was dissolved in 50 ml of absolute ethanol and dechlorinated on a Parr hydrogenation apparatus using 5% Pd/C catalyst. After removal of the catalyst, the solvent was evaporated, and the residue neutralised with 50 ml of 0.5M sodium bicarbonate, and extracted twice with 50 ml of methylene chloride. The extract was dried over MgSO$_4$, filtered, and evaporated, giving 1.35 g (88%) of (B), m.p. 68°–72°. NMR: (CDCl$_3$) 2.52 (s, 3, Me), 4.03 (s, 3, OMe), 6.9–7.05 (m, 1, Ar), 7.18 (d, 1, pyr-beta-H, J=4.5 Hz), 7.45 (m, 2, ArH$_2$), 8.73 (d, 1, pyr-alpha-H, J=4.5 Hz). Anal. Calcd. for C$_{11}$H$_{11}$NO: C, 76.28; H, 6.40; N, 8.09. Found: C, 76.00; H, 6.73; N, 7.74.

C. 1,2,3,4-Tetrahydro-8-methoxy-4-methylquinoline

The product of B, 1.25 g was reduced in 40 ml of absolute ethanol using 4 equivalents of sodium cyanoborohydride plus 4 equivalents of concentrated hydrochloric acid. The reaction was stirred at room temperature for 1 hour, heated at 60° for two hours, and then allowed to stir overnight at room temperature. The reaction mixture was made basic with ammonia, diluted with 50 ml of water, and extracted three times with 75 ml portions of methylene chloride, followed by drying the extracts and removal of the solvent. The residual orange oil, 1.26 g. was purified on a silica gel column using 2% ethyl acetate in heptane, which produced a light yellow oil, 0.95 g (74%) of C. NMR: (CDCl$_3$) δ 1.25 (d, 3, Me, J=7 Hz), 1.6–2.3 (m, 2, C$^3$H$_2$), 2.6–3.2 (m, 1, C$^4$—H), 3.27 (tr, 2, C$^2$H$_2$, J=5.5 Hz), 3.74 (s, 3, OMe), 4.07 (br, 1, NH), 6.53 (m, 3, ArH$_3$). Anal. Calcd. for C$_{11}$H$_{15}$NO: C, 74.54; H, 8.53; N, 7.90. Found: C, 74.57; H, 8.57; N, 7.81.

D. 2,4-Diamino-5-(1,2,3,4-tetrahydro-8-methoxy-4-methyl-6-quinolylmethyl)pyrimidine The procedure of Example 1 was used to react product C (0.86 g) with 2,4-diamino-5-hydroxymethylpyrimidine in acetic acid, with 2 equivalents of hydrochloric acid. The reaction was refluxed for 3.5 hours, the solvent removed, and the residue dissolved in water and made basic with ammonia, followed by extraction with methylene chloride. The extract was purified on a silica gel column which was eluted with methylene chloride:methanol/19:1, giving 1.20 g (93%) of the title compound. A portion was converted to the dihydrochloride salt with ethanol-hydrochloric acid; m.p. 221°–223°. Anal. Calcd. for C$_{16}$H$_{21}$N$_5$O.2HCl.H$_2$O: C, 49.24; H, 6.46; N, 17.94. Found: C, 49.34; H, 6.48; N, 17.92.

EXAMPLE 8

2,4-Diamino-5-(8-methoxy-6-quinolylmethyl)pyrimidine

The product of Example 2 was oxidised using 20% palladium on charcoal in 50 ml of cumene, by heating at 150° C. for 21 hours. After the catalyst was removed and the solvent evaporated, the residue was purified on a silica gel column which was eluted with methylene chloride:methanol/19:1. This produced 0.51 g (35%) of the title compound, which melted at 285°–287° after recrystallisation from betamethoxyethanol. Anal. Calcd. for C$_{15}$H$_{15}$N$_5$O: C, 64.04; H, 5.37; N, 24.89. Found: C, 63.88; H, 5.37; N, 24.84.

EXAMPLE 9

2,4-Diamino-5-(8-(2-methoxyethoxy)-6-quinolylmethyl)pyrimidine

The product of Example 3 was oxidised in the manner of Example 8, and purified similarly. After recrystallisation from beta-methoxyethanol, there was obtained 0.18 g (20%) of title compound, melting at 253°–255° C. Anal. Calcd. for C$_{17}$H$_{19}$N$_5$O$_2$: C, 62.76; H, 5.89; N, 21.52. Found: C, 62.58; H, 5.92; N, 21.45.

EXAMPLE 10

2,4-Diamino-5-(8-methoxy-4-methyl-6-quinolylmethyl)pyrimidine

The product of Example 7 was oxidised in the manner described in Example 8. The product was recrystallised from betamethoxyethanol, giving 0.11 g (17%) of the title compound, which melted at 287°–290°. Anal. Calcd. for C$_{16}$H$_{17}$N$_5$O; C, 65.07; H, 5.80; N, 23.71. Found: C, 65.01; H, 5.83; N, 23.69.

EXAMPLE 11

2,4-Diamino-5-(4-methyl-6-quinolylmethyl)pyrimidine

The product of Example 4 was oxidised in the manner of Example 8, and purified similarly. After recrystallisation from beta-methoxyethanol, there was obtained 1.44 g (55%) of the title compound, melting at 262°–268° C. NMR: (Me$_2$SO-d$_6$) δ 2.64 (s, 3, Me), 3.83 (s, 2, CH$_2$), 5.70 (br s, 2, NH$_2$), 6.16 (br s, 2, NH$_2$), 7.33 (d, 1, pyridine-beta H, J=4.5), 7.56 (dd, 1, ArH$^7$, J=2.8), 7.59 (s, 1, pyrimidine-H$^6$), 7.92 (d, 1, ArH$^8$, J=8.8), 7.98 (d, 1, ArH$^5$, J=1.6), 8.68 (d, 1, pyridine-alpha H, J=4.4). Anal. Calcd. for C$_{15}$H$_{15}$N$_5$: C, 67.91; H, 5.70; N, 26.40. Found: C, 67.82; H, 5.74; N, 26.35.

EXAMPLE 12

2,4-Diamino-5-(4-methyl-8-nitro-6-quinolylmethyl)-pyrimidine

The product of Example 11 (0.53 g, 2 mmol) was dissolved in 7 ml of concentrated sulfuric acid, and chilled to 0°. Then 0.3 ml (6.4 mmol) of fuming nitric acid (d=1.5) in 0.5 ml of concentrated sulfuric acid was added dropwise to the solution. The reaction was stirred at 0°–5° for 30 minutes, then at 25° for 1 hour. It was then poured onto 50 ml of ice and neutralised to pH 9 with concentrated ammonium hydroxide. The precipitate which formed was filtered and dried, and then purified on a silica gel column which was eluted with methylene chloride:methanol/12:1, giving 0.33 g (53%) of the title compound, which melted at 256°–258° after recrystallisation from beta methoxyethanol:water/2:1. NMR (Me$_2$SO-d$_6$) δ 2.72 (s, 3, Me), 3.90 (s, 2, CH$_2$), 5.77 (br s, 2, NH$_2$), 6.24 (br s, 2, NH$_2$), 7.55 (d, 1, pyridine-beta H, J=4.1), 7.71 (s, 1, pyrimidine-H$^6$), 8.05 (d, 1, ArH$^5$, J=1.8), 8.28 (d, 1, ArH$^7$, J=1.6), 8.81 (d, 1, pyridine-alpha H, J=4.4). Anal. Calcd. for C$_{15}$H$_{14}$N$_6$O$_2$0.5H$_2$O: C, 56.42; H, 4.73; N, 26.32. Found: C, 56.34; H, 4.82; N, 26.21.

EXAMPLE 13

2,4-Diamino-5-(5,6,7-trimethoxy-2-naphthylmethyl)-pyrimidine hydrochloride

A. 5,6,7-Trimethoxynaphthalene-2-carboxaldehyde

Methyl 5,6,7-trimethoxynaphthalene-2-carboxylate (C. L. Chen, F. D. Hostettler, Tetrahedron, 1969, 25, 3223) was reduced to the aldehyde in the following manner. Sodium bis(2-methoxyethoxy)aluminium hydride in toluene (5.6 ml, 20 mmol, 70% solution) was chilled to −20° C. under nitrogen in 20 ml of dry toluene and then 1.74 ml (20 mmol) of morpholine in 5 ml of toluene was added dropwise to it. The reaction was allowed to stir at −5° for 30 minutes, after which it was rechilled to −20° and added slowly to a solution of methyl 5,6,7-trimethoxynaphthalene-2-carboxylate (2.76 g, 10 mmol) in 20 ml of toluene at −20°. The reaction was stirred for 30 minutes at −10°, then rechilled to −20°, basified with 20 ml (40 mmol) of 2N sodium hydroxide, and extracted with three times 25 ml of toluene. The combined toluene layers were washed with 50 ml of 1N hydrochloric acid, then with 50 ml of 0.5M sodium bicarbonate, and finally with 50 ml of water, and dried over magnesium sulfate, filtered and evaporated to give 2.55 g (52% crude yield) of the title compound. This was purified on a silica gel column eluting with hexane:ethyl acetate/12:1 to give 2.15 g (44%) of the product, m.p. 96°–98°. Anal. Calcd. for $C_{14}H_{14}O_4$: C, 68.28; H, 5.73. Found: C, 68.16; H, 5.78.

B. 2,4-diamino-5-(5,6,7-trimethoxy-2-naphthylmethyl)pyrimidine hydrochloride

The aldehyde from above was converted to 2-(5,6,7-trimethoxy-2-naphthylmethyl)-3-anilinoacrylonitrile on a 8 mmol scale in the same manner as Example 5-A. The crude product from this reaction was cyclised with guanidine hydrochloride and sodium methylate in ethanol as in Example 5-B to give the title compound as the free base, 0.74 g (27% yield). This was recrystallised from ethanol plus an equivalent of hydrochloric acid, 0.26 g, mp 252°–254°. Anal. Calcd. for $C_{18}H_{20}N_4O_3HCl$: C 57.37; H, 5.62; N, 14.87; Cl, 9.41. Found: C, 57.11; H, 5.67; N, 14.79; Cl, 9.31.

EXAMPLE 14

2,4-Diamino-5-(8-methoxy-2,4-dimethyl-6-quinolylmethyl)pyrimidine

A. 2,4-diamino-5-(3-methoxy-4-aminobenzyl)pyrimidine

A solution of 6.30 g (0.045 mol) of 2,4-diamino-5-hydroxymethylpyrimidine, 6.15 g (0.05 mol) of o-anisidine and 3.75 ml of concentrated hydrochloric acid in 55 ml of glacial acetic acid was heated to reflux for 6 hours. The mixture was stirred at room temperature overnight. The solvent was removed under vaccum and the residue was taken up in water, made basic with ammonium hydroxide, and the aqueous solution was extracted with dichloromethane:methanol/3:1. The organic layers were combined, dried and concentrated to a purple glass. This was purified on a silica gel column to give 7.81 g of the 4-N-acetylated product.

This product was dissolved in 400 ml of 2N sodium hydroxide and heated to reflux for a total of 6 hours. The mixture was cooled and the solid was filtered. This was dissolved in water, taken to pH 8.5, and the aqueous solution was extracted with dichloromethane. The organic extract was dried and concentrated to give 4.0 g of the title compound; m.p. 210°–212° C. Anal. Calcd for $C_{12}H_{15}N_5O$: C, 58.76; H, 6.16; N, 28.55. Found: C, 58.66; H, 6.22; N, 28.48.

B. 2,4-Diamino-5-(8-methoxy-2,4-dimethyl-6-quinolylmethyl)pyrimidine

To a solution of 1,5 g (0.006 mol) of the product from A in 30 ml of 95% ethanol, 0.5 ml of concentrated hydrochloric acid, and 2.43 g (0.0089 mol) of ferric chloride hydrate was added 0.5 g (0.006 mol) of 3-penten-2-one. Following the dropwise addition the solution was refluxed for 6 hours. The solvent was removed under vaccum and the residue was dissolved in water and neutralised with ammonium hydroxide. The black solid which precipitated was collected by filtration. Purification on a silica gel column followed by recrystallisation from ethanol gave 0.1094 g (5.88%) of the title compound; m.p. 289°–290° C. Anal Calcd for $C_{17}H_{19}N_5O$: C, 66.00; H, 6.19; N, 22.64. Found: C, 65.75; H, 6.26; N, 22.56.

EXAMPLE 15

2,4-Diamino-5-(8-chloro-1,2,3,4-tetrahydro-2,4-dimethyl-6-quinolylmethyl)pyrimidine hemihydrate A. 8-chloro-2,4-dimethylquinoline To 4.0 g (0.03 mol) of o-chloroaniline in 50 ml of hydrochloric acid at 100° C. was added dropwise 3.4 g (0.04 mol) of 3-penten-2-one. The mixture was refluxed for 12 hours, then neutralised with 5N sodium hydroxide and extracted with dichloromethane. The organic extract was dried and concentrated to an oil. This was purified on a silica gel column to give 2.54 g (42% of the title product; m.p. 66°–68° C. Anal. Calcd. for $C_{11}H_{10}NCl$: C, 68.94; H, 5.26; N, 7.31; Cl, 18.50. Found C, 68.87; H, 5.27; N, 7.29; Cl, 18.48.

B. 1,2,3,4-Tetrahydro-8-chloro-2,4-dimethylquinoline

To 1.7 g (0.0088 mol) of the product from A dissolved in 25 ml of ethanol was added 2.23 g (0.035 mol) of sodium cyanoborohydride and 3.5 g of concentrated hydrochloric acid. After heating 1 hour at 80°, one equivalent more of each of sodium cyanoborohydride and acid were added and the mixture was heated at 80° for 1 hour longer. Water was added, the reaction mixture was made basic with ammonium hydroxide, and extracted with dichloromethane. The organic extract was dried and concentrated to an oil. This was purified on a short silica gel column to give 1.23 g of the title compound.

C. 2,4-Diamino-5-(8-chloro-1,2,3,4-tetrahydro-2,4-dimethyl-6-quinolylmethyl)pyrimidine hemihydrate A mixture of 0.9 g (0.0046 mol) of the product from B, 0.6 g (0.0043 mol) of 2,4-diamino-5-hydroxymethyl pyrimidine, 0.8 ml of concentrated hydrochloric acid, and 10 ml of glacial acetic acid was heated under reflux for 6 hours. The solvent was removed under vacuum, the residue was dissolved in water and made basic with ammonium hydroxide. The gummy solid which resulted was extracted with dichloromethane:methanol/3:1. The extracts were dried and evaporated to leave a green crystalline solid (1.22 g). Purification on a short silica gel column followed by recrystallisation gave 0.058 g of the title compound; m.p. 195°–197° C. Anal. Calcd. for $C_{16}H_{20}N_5Cl \cdot \frac{1}{2} H_2O$: C, 58.80; H, 6.48; N, 21.43; Cl, 10.85. Found: C, 58.75; H, 6.47; N, 21.39; Cl, 10.83.

EXAMPLE 16

2,4-Diamino-5-(1,2,3,4-tetrahydro-N-methyl-6-quinolylmethyl)pyrimidine

A. 1,2,3,4-Tetrahydro-N-methylquinoline 1,2,3,4-Tetrahydroquinoline (6.66 g, 50 mmol) was added to 40 ml of water, 40 ml of ethyl acetate, and 5.04 g (60 mmol) of sodium bicarbonate to which was added 5.68 ml (60 mmol) of dimethylsulfate dropwise. The reaction was stirred at room temperature for 2½ hours, and the organic layer was separated. The aqueous layer was extracted with ethyl acetate, then the organic layers were combined and evaporated to give 4.56 g (62% yield) of the title compound. NMR (CDCl$_3$) δ 1.93 (quintet, 2, CH$_2$), 2.74 (tr, 2, CH$_2$), 2.81 (s, 3, NMe), 3.17 (tr, 2, CH$_2$), 6.55 (m, 2, Ar), 6.97 (m, 2, Ar).

B. 2,4-Diamino-5-(1,2,3,4-tetrahydro-N-methyl-6-quinolylmethyl)pyrimidine

The product from above (0.86 g, 5.8 mmol) and 0.82 g (5.8 mmol) of 2,4-diamino-5-hydroxymethylpyrimidine were dissolved in 10 ml of glacial acetic acid and 0.5 ml of concentrated hydrochloric acid and refluxed for 1 hour. The solvent was evaporated, and the residue was dissolved in water and basic with ammonium hydroxide to pH 9. The aqueous layer was extracted with methylene chloride:methanol/3:1, which was dried and evaporated to give 1.53 g of the crude product. This was purified on a silica gel column eluted with methylene chloride:methanol/19:1, followed by recrystallisation to give 1.07 g (68% yield) of the title compound, mp 190°-191° (absolute ethanol). NMR: (Me$_2$SO-d$_6$) δ 1.84 (quintet, 2, CH$_2$), 2.63 (tr, 2, CH$_2$), 2.77 (s, 3, NMe), 3.11 (tr, 2, NCH$_2$), 3.41 (s, 2, pyrimidine-CH$_2$), 5.63 (br s, 2, NH$_2$), 5.93 (br s, 2, NH$_2$), 6.47 (d, 1, ArH$^8$), 6.73 (d, 1, ArH$^5$), 6.84 (dd, 1 ArH$^7$), 7.44 (s, 1, pyrimidine-H$^6$). Anal. Calcd. for C$_{15}$H$_{19}$N$_5$: C, 66.89; H, 7.11; N, 26.00. Found: C, 66.84; H, 7.13; N, 25.95.

EXAMPLE 17

2,4-Diamino-5-(N-ethyl-1,2,3,4-tetrahydro-4-methyl-6-quinolylmethyl)pyrimidine dihydrochloride hydrate A. N-Ethyl-1,2,3,4-tetrahydro-4-methylquinoline 4-Methylquinoline (lepidine) (1.43 g, 10 mmol) and 50 ml of glacial acetic acid were added together and cooled to 10° C. Sodium cyanoborohydride (2.64 g, 42 mmol) was added gradually, and the reaction was stirred at 25° for 2 hours, and then heated at 55° for 1½ hours. After stirring overnight at 25°, the reaction was neutralised with concentrated ammonium hydroxide to pH 10.5, and then the product was extracted into methylene chloride and evaporated. The crude product was purified on a silica gel column eluting with hexane to give 0.55 g (31% yield) of the title compound. MS: 175 (M+), 160 (M+-Me); NMR: CDCl$_3$ δ 1.22 (tr, J=7 Hz, 3, NCH$_2$Me), 1.30 (d, J=3.5, 3, CHMe), 1.5-2.3 (m, 2, CH$_2$), 2.89 (sextet, 1, CHMe), 3.29 (tr, 2, NCH$_2$), 3.30 (quartet, 2, NCH$_2$Me), 6.59 (m-tr, 2, Ar), 7.10 (m-tr, 2, Ar).

B. 2,4-Diamino-5-(N-ethyl-1,2,3,4-tetrahydro-4-methyl-6-quinolylmethyl)-pyrimidine dihydrochloride hydrate The product from above (0.38 g, 2.2 mmol) was condensed with 2,4diamino5-hydroxymethylpyrimidine as in Example 17. The crude product from the reaction was purified on a silica gel column eluted with methylene chloride:methanol/19:1, giving 0.53 g of product (83% yield). This was recrystallised from absolute ethanol with two equivalents of hydrochloric acid to give 0.16 g of the title compound, mp 250°-252°. NMR: (Me$_2$SO-d$_6$) (free base from column) δ 1.02 (tr, 3, NCH$_2$Me), 1.15 (d, 3, CHMe), 1.6-1.85 (m, 2, CH$_2$), 2.72 (m, 1, CHMe), 3.15 (m, 4, NCH$_2$, NCH$_2$Me), 3.42 (s, 2, pyrimidine-CH$_2$), 5.61 (br s, 2, NH$_2$), 5.94 (br s, 2, NH$_2$), 6.48 (d, J=9 Hz, 1, ArH$^8$), 6.81 (dd, J=2, 9 Hz, 1, ArH$^7$), 6.84 (d, J=2 Hz, 1, ArH$^5$), 7.44 (s, 1, pyrimidine-H$^6$). Anal. Calcd. for C$_{17}$H$_{23}$N$_5$.2HCl.H$_2$O: C, 52.58; H, 7.01; N, 18.03; Cl, 18.25. Found: C, 52.63; H, 7.03; N, 18.01; Cl, 18.10.

EXAMPLE 18

2,4-Diamino-5-(8-amino-4-methyl-6-quinolylmethyl)-pyrimidine dihydrochloride

The product of Example 12 (0.78 g, 2.5 mmol) was dissolved in 35 ml of β-methoxyethanol, and then 0.06 g of 5% Pd/C and 0.3 ml of 95% hydrazine were added, and the reation was refluxed for 1 hour. The Pd/C was filtered off, the solvent removed, and the product was purified on a silica gel column which was eluted with 7% methanol in methylene chloride. This gave 0.48 g (69% yield) of the free base which was recrystallised as the dihydrochloride salt from ethanol, mp 303°-305° dec. Anal. Calcd. for C$_{15}$H$_{16}$N$_6$.2HCl.0.5H$_2$O: C, 49.73; H, 5.29; N, 23.20; Cl, 19.57. Found: C, 49.71; H, 5.30; N, 23.18; Cl, 19.51.

EXAMPLE 19

2,4-Diamino-5-(5-amino-4-methyl-6-quinolylmethyl)-pyrimidine dihydrochloride

When the product of Example 11 was nitrated and only partially purified by a silica gel column without recrystallisation, and then reduced as in Example 18, a second amino-quinoline product was detected and isolated from a column. On a 2.5 mmol scale, there was obtained 0.235 g (32%) of the title compound, mp 290° dec. (HCl in absolute ethanol). NMR of the free base: (Me$_2$SO-d$_6$) δ 2.96 (s, 3, Me), 3.60 (s, 2, CH$_2$), 5.08, 5.70, 6.14 (3 broad bands, 6, (NH$_2$)$_3$), 6.99 (d, J=8 Hz, 1, Ar), 7.16 (d, J=8 Hz, 1, Ar), 7.24 (s, 1, pyrm-H$_6$), 7.27 (d, J=4 Hz, 1, pyr-H), 8.51 (d, J=4 Hz, 1, pyr-H). Anal. Calcd. for C$_{15}$H$_{16}$N$_6$.2HCl: C, 51.00; H, 5.14; N, 23.79; Cl, 20.07. Found: C, 50.95; H, 5.17; N, 23.72; Cl, 19.97.

EXAMPLE 20

2,4-Diamino-5-(1,2,3,4-tetrahydro-8-methoxy-1,4-dimethyl-6-quinolylmethyl)-pyrimidine dihydrochloride A. 1,2,3,4-Tetrahydro-8-methoxy-1,4-dimethylquinoline The product of Example 7-C (1,2,3,4-tetrahydro-8-methoxy-4-methylquinoline) was methylated by dissolving the compound (0.71 g, 4 mmol) in 15 ml of tetrahydrofuran under nitrogen, chilling to 0° C., and then 1.14 g (30 mmol) of sodium borohydride was added, followed by a slow addition of 12 ml of formic acid. The reaction was allowed to warm to room temperature, and then it was stirred overnight. The solvent was removed, the residue was slurried in water and basified to pH 9 with ammonium hydroxide and extracted into methylene chloride. The product was purified on a silica gel column which was eluted with hexane:ethyl acetate/19:1 giving a light brown oil. Anal. Calcd. for C$_{12}$H$_{17}$NO: C, 75.35; H, 8.96; N, 7.32. Found: C, 75.44; H, 8.98; N, 7.28.

B. 2,4-Diamino-5-(1,2,3,4-tetrahydro-8-methoxy-1,4-dimethyl-6-quinolylmethyl)pyrimidine dihydrochloride The product from above (0.5 g, 2.6 mmol) was condensed with 2,4-diamino-5-hydroxymethylpyrimidine as in Example 17 and 18. The product was worked up as before in Example 17, and then purified on a silica gel column which was eluted with methylene chloride:methanol/19:1 giving 0.27 g (33% yield) of the title compound as the free base as well as recovering 0.17 g of unreacted tetrahydroquinoline starting material (34%). The product was recrystallised from absolute ethanol as the dihydrochloride, mp 219°-221°. Anal. Calcd for C$_{17}$H$_{23}$N$_5$0.2HCl.0.5H$_2$O: C, 51.65; H, 6.63; N, 17.71; Cl, 17.94. Found: C, 51.58; H, 6.64; N, 17.66; Cl, 17.87.

EXAMPLE 21

Ethyl 6-(2,4-diamino-5-pyrimidinylmethyl)-1,2,3,4-tetrahydro-5,8-dimethoxy-3-quinolinecarboxylate A. Ethyl 1,2,3,4-tetrahydro-5,8-dimethoxy-3-quinolinecarboxylate Ethyl 5,8-dimethoxy-3-quinolinecarboxylate was formed as described in the literature (E. H. Erickson, C. F. Hainline, L. S. Lenon, et al. J. Med. Chem. 1979, 22, 816). 2,5-Dimethoxyaniline and diethyl ethoxymethylenemalonate condense and then cyclise at high temperature (250°) in diphenyl ether to form ethyl 1,4- dihydro-5,8-dimethoxy-4-oxo-3-quinolinecarboxylate which is chlorinated at the 4-position with phosphorus oxychloride to give ethyl 4-chloro-5,8-dimethoxy-3-quinolinecarboxylate. The dehalogenation of this quinoline (20.34 g, 0.069 mol) in 150 ml of absolute ethanol with 1 g of 5% Pd/C and 22.53 ml of triethylamine (0.156 mol) was done with a Parr hydrogenator apparatus which gave the correct product, ethyl 5,8-dimethoxy-3-quinolinecarboxylate, as well as the 1,4-dihydro and the 1,2,3,4-tetrahydro quinoline products. This result of further reduction to the 1,4-dihydro product was indicated in the article listed above on page 817, but the formation of the 1,2,3,4-tetrahydro product had not been mentioned there. These three quinoline products were separated on a silica gel column which was eluted with hexane, followed by hexane:ethyl acetate/4:1 and 1:1, giving 0.46 g (2.6% yield) of the title compound, NMR: CDCl$_3$ δ1.23 (tr, 3, CH$_2$Me), 2.94 (br-m, 2, CH$_2$), 3.2–3.6 (m, 3, CH$_2$, CH), 3.76 (s, 6, (OMe)$_2$), 4.21 (quartet, 2, CH$_2$Me), 4.2 (br, 1, NH), 6.12 (d, 1, Ar), 6.57 (d, 1, Ar); 3.31 g of the 1,4-dihydro quinoline product (18.5%), NMR: CDCl$_3$ δ 1.28 (tr, 3, CH$_2$Me), 3.61 (s, 2, CH$_2$), 3.73 (s, 6, (OMe)$_2$), 4.19 (quartet, 2, CH$_2$Me), 6.2–6.7 (br, 1, NH), 6.29 (d, 1, Ar), 6.60 (d, 1, Ar), 7.32 (d, 1, pyr-H); and 2.04 g (11%) of the ethyl 5,8-dimethoxy-3-quinolinecarboxylate.

B. Ethyl 6-(2,4-diamino-5-pyrimidinylmethyl)-1,2,3,4-tetrahydro-5,8-dimethoxy-3-quinolinecarboxylate Ethyl-1,2,3,4-tetrahydro-5,8-dimethoxy-3-quinolinecarboxylate (0.38 g, 1.43 mmol) was reacted with 2,4-diamino-5-hydroxymethylpyrimidine as in Example 17, and the product worked up as before. The product was purified on a silica gel column eluted with methylene chloride:methanol/19:1 to give 0.27 g (49%) of the title compound, mp 186°–188° (absolute ethanol). Anal. Calcd. for C$_{19}$H$_{25}$N$_5$O$_4$: C, 58.90; H, 6.50; N, 18.08. Found: C, 58.95; H, 6.52; N, 18.08.

EXAMPLE 22

2,4-Diamino-5-(4,8-dimethoxy-2-methyl-6-quinolylmethyl)primidine

A. 4-Bromo-2-methoxyaniline

2-Methoxyaniline (o-anisidine) (15 g, 0.122 mol) was brominated with 2,4,4,6-tetrabromo-2,5-cyclohexadienone (50 g, 0.122 mol) by dissolving the aniline in 250 ml of methylene chloride, chilling the solution to −10°, and slowly adding and brominating agent, keeping the temperature below −5°. The reaction was allowed to warm at room temperature, and then washed with 2N sodium hydroxide (2×75 ml), then washed with water (2×25 ml), dried over magnesium sulfate, and evaporated to dryness. The product was purified on a silica gel column, eluted with methylene chloride giving 23.68 g (96%) of the title compound, mp 56.5°–58° (petroleum ether). Anal. Calcd for C$_7$H$_8$BrNO: C, 41.61; H, 3.99; Br, 39.55; N, 6.93. Found: C, 41.59; H, 3.99; Br, 39.49; N, 6.92.

B. Ethyl 3-(4-bromo-2-methoxyphenylimino)butyrate

The product from above (5.25 g, 26 mmol) and ethyl acetoacetate (3.39 g, 26 mmol) were added together in 20 ml of absolute ethanol with 0.06 ml of glacial acetic acid and 7 g of drierite and refluxed for 4 hours. The drierite was filtered off, the solvent removed, andd the product was purified on a silica gel column eluted with hexane:ethyl acetate/19:1 to give 6.47 g (79%) of the title compound as a colourless oil. NMR: CDCl$_3$ δ1.28 (tr, 3, CH$_2$Me), 1.97 (s, 3, =CH—Me), 3.85 (s, 3, OMe), 4.17 (quartet, 2, CH$_2$Me), 4.75 (s, 1, =CH), 7.00 (s, 3, Ar). Anal. Calcd. for C$_{13}$H$_{16}$BrNO$_3$: C, 49.70; H, 5.13; N, 4.46. Found: C, 49.52; H, 5.16; N, 4.43.

C. 6-Bromo-4-hydroxy-8-methoxy-2-methylquinoline

The product from above (6.32 g, 20.1 mmol) was cyclised in diphenyl ether (30 ml) when heated at 255° for 25 minutes. The product precipitated out of the diphenyl to give 3.80 g (70.5%) which was washed well with diethyl ether, and then recrystallised from absolute ethanol, mp 293°–296°. Anal. Calcd. for C$_{11}$H$_{10}$BrNO$_2$: C, 49.28; H, 3.76; N, 5.22. Found: C, 49.17; H, 3.78; N, 5.21.

D. 6-Bromo-4-chloro-8-methoxy-2-methylquinoline

The product from above (2.79 g, 10.4 mmol) was chlorinated by refluxing with 13 ml of phosphorus oxychloride at 120° for 2 hours, neutralised with 8 ml of ammonium hydroxide in 100 ml of ice to pH 9, and extracted into methylene chloride. The crude product was purified on a silica gel column eluted with hexane:ethyl acetate/5:1 to give 2.76 g (93%) of the title compound, mp 140°–142°. Anal. Calcd for C$_{11}$H$_9$BrClNO: C, 46.11; H, 3.17; N, 4.89. Found: C, 46.04; H, 3.19; N, 4.88.

E. 6-Bromo-4,8-dimethoxy-2-methylquinoline

The product from above (0.85 g, 3.0 mmol) was dissolved in 40 ml of methanol with 0.8 g (15 mmol) of sodium methylate and heated in a steel bomb at 120° for 5 hours. The solvent was removed, water added, and the product was extracted into methylene chloride and then purified on a silica gel column, eluting with hexane:ethyl acetate/1:3 to give 0.72 g (86%), mp 167°–168°. Anal. Calcd. for C$_{12}$H$_{12}$BrNO$_2$: C, 51.09; H, 4.29; N, 4.96. Found: C, 50.95; H, 4.34; N, 4.90.

F. 6-Formyl-4,8-dimethoxy-2-methylquinoline

The product from above (0.67 g, 2.4 mmol) was dissolved in 25 ml of dry tetrahydrofuran and chilled to −70° under nitrogen. Then 1.63 ml (1.1 equiv.) of 1.6M n-butyl lithium in hexane was added dropwise via a syringe, and the reaction was stirred for 2 minutes followed by the addition of 0.21 g (1.2 equiv) of dry dimethylformamide. The reaction was allowed to warm to −40°, and then it was quenched with 8 ml of 1N hydrochloric acid. The reaction was extracted with ether, the aqueous was basified to pH 12 with 1N sodium hydroxide and extracted into methylene chloride and evaporated to dryness. The product was purified on a silicagel column which was eluted with 2% methanol in methylene chloride to give 0.33 g (60%) of the title compound, NMR:CDCl$_3$δ2.23 (s, 3, Me), 4.01 (s, 3, OMe), 4.06 (s, 3, OMe), 6.70 (s, 1, pyr-βH), 7.40 (d, 1, Ar), 8.14 (d, 1, Ar), 9.98 (s, 1, CHO).

G. 2,4-Diamino-5-(4,8-dimethoxy-2-methyl-6-quinolylmethyl)pyrimidine

The aldehyde from above was converted to 2-(4,8dimethoxy-2-methyl-6-quinolylmethyl)-3-anilinoacrylonitrile with anilinopropionitrile and sodium methylate in dimethyl sulfoxide on a 1.4 mmol scale in the same manner as in Example 5-A. The crude product from this reaction was condensed with guanidine hydrochloride and sodium methylate in ethanol as in Example 5-B to give the crude product.

EXAMPLE 23

2,4-Diamino-5-(4-dimethylamino-8-methoxy-2-methyl-6-quinolylmethyl)pyrimidine

A. 6-Bromo-4-dimethylamino-8-methoxy-2-methylquinoline

The product from Example 22-D (1.0 g, 3.45 mmol) was dissolved in 50 ml of a 10% solution of dimethylamine in ethanol (5 g/50 ml), and heated in a steel bomb at 120° for 5 hours. The reaction was worked up as in Example 22-E and purified on a silica gel column which was eluted with hexane:ethyl acetate/1:4 to give 0.89 g (89%) of the title compound, m.p. 115°–117°. Anal. Calcd. for $C_{13}H_{15}BrN_2O$: C, 52.90; H, 5.12; N, 9.49. Found: C, 52.85; H, 5.16; N, 9.48.

B. 4-Dimethylamino-6-formyl-8-methoxy-2-methylquinoline

The product from above (0.78 g, 2.6 mmol) was formylated as in Example 22-F to give the title compound, mp 127°–129°. Anal. Calcd. for $C_{14}H_{16}N_2O_2\cdot\frac{1}{3}H_2O$: C, 67.18; H, 6.71; N, 11.19. Found: C, 67.40; H, 6.67; N, 11.00.

C. 2,4-Diamino-5-(4-dimethylamino-8-methoxy-2-methyl-6-quinolylmethyl)pyrimidine The aldehyde from above was condensed with anilinopropionitrile as in Example 22-G, followed by the reaction with guanidine to give the crude product. This was purified on a silica gel column which was eluted with methylene chloride:methanol/4:1 to give the title compound, MS 338(M+).

EXAMPLE 24

2,4-Diamino-5-(2-dimethylamino-4-methyl-6-quinolylmethyl)-pyrimidine

A. N-(4-Bromophenyl)-3-oxobutyramide

To a stirred solution of 34.14 g (0.200 moles) of 4-bromoaniline in 130 ml toluene under $N_2$, 18.00 g (0.220 moles) of diketene was added dropwise over a 10 minute period followed by 15 ml of toluene. The temperature rose to 80° C. during the addition; the solution was then refluxed 20 minutes, cooled to 55° C. and 60 ml of petroleum ether added. An immediate precipitation occurred. The tan-white crystals were filtered and washed with three 100 ml portions of 1:1 toluene/petroleum ether. The product was taken up in hot absolute ethanol and crystallisation induced by addition of toluene to the ethanolic solution. Three crops of crystals from the ethanol/toluene solvent system gave 22.90 g (43%) and had $R_f$ 0.69 on silica TLC with ethyl acetate; mp 135.8°–137.2° C. Anal. Calcd. for $C_{10}H_{10}BrNO_2$: C, 46.90; H, 3.94; N, 5.47; Br, 31.20. Found: C, 47.13; H, 4.00; N, 5.46; Br, 31.31.

B. 6-Bromo-4-methyl-2-(1H)-quinolinone

A mixture of 3.00 g (0.0117 moles) of N-(4-bromophenyl)-3-oxobutyramide and 6 ml concentrated sulfuric acid was stirred and heated to 95°–100° C. ($H_2O$ bath) for 1½ hours. The resulting solution was poured onto an ice/$H_2O$ mixture to yield a white crystalline product. The crystals were collected and taken up in 200 ml absolute ethanol. The volume was reduced to 150 ml followed by chilling; crystals were isolated (0.71 g 25.6%), mp 292°–299° C. Anal. Calcd. for $C_{10}H_8BrNO$: C, 50.45; H, 3.39; N, 5.88; Br, 33.56. Found: C, 50.28; H, 3.44; N, 5.83; Br, 33.68. A TLC of the product on silica showed $R_f$ 0.18 with ethyl acetate eluent.

C. 6-Bromo-2-chloro-4-methylquinoline

A 0.46 g, (0.0019 mole) sample of 6-bromo-4-methyl-2-(1H)-quinolinone was dissolved in 3.0 ml $POCl_3$ under $N_2$ with stirring and heated to reflux for 2 hours. The solution solidified into a purple gum; 2.0 ml of extra $POCl_3$ was added to dissolve the solid. The solution was then slowly poured onto a vigorously stirred slurry of 8 ml concentrated $NH_4OH$ and approximately 75 g of ice. An immediate pink crystalline solid formed. The slurry was transferred to a separatory funnel and extracted with five 30 ml portions of $CH_2Cl_2$. The extracts were washed with two 40 ml portions of water and dried over $MgSO_4$. The solvent was removed under vacuum, leaving a rusty red crystalline solid, 0.48 g (97%). The product was taken up in hot absolute ethanol, Norite A decolourising carbon added, and filtered through Celite to yield a yellow liquid. Slow cooling of the ethanolic solution gave very fine, pink crystals, m.p. 139.1°–139.80° C. TLC showed $R_f$ 0.25 on silica with 1:1 hexane:$CH_2Cl_2$ eluent. Anal. Calcd. for $C_{10}H_7BrClN$: C, 46.82; H, 2.75; N, 5.46; Br, 31.15; Cl, 13.82. Found: C, 46.97; H, 2.79; N, 5.42; Br, 31.08; Cl, 13.79.

D. 6-Bromo-2-dimethylamino-4-methylquinoline

A solution of 0.26 g (0.00101 mole) of 6-bromo-2-chloro-4-methylquinoline in 50 ml absolute ethanol was placed in a glass bomb liner, cooled to −78° C., and 7.19 g (0.159 mole) of dimethylamine bubbled into the cold ethanolic solution. The mixture was heated to 112° in a sealed autoclave for 3 hours. The solvent and excess dimethylamine were then removed under vacuum, to leave 0.36 g of residue, which was washed with 40 ml $H_2O$ to remove the $(CH_3)_2NH\cdot HCl$. The product was then taken up in 40 ml absolute ethanol, treated with Norite A alkaline decolourising carbon and filtered through Celite followed by concentration and addition of 7 ml $H_2O$ to induce crystallisation after chilling, the product collected was a light yellow crystalline solid, 0.20 g (74.3%), m.p. 81.9°–84.1° C., and $R_f$ 0.11 on silica with 1:1 $CH_2Cl_2$:hexane.

Anal. Calcd. $C_{12}H_{13}BrN_2$: C, 54.36; H, 4.94; N, 10.56; Br, 30.14. Found: C, 54.29; H, 4.98; N, 10.54; Br, 30.18

E. 2-Dimethylamino-6-formyl-4-methylquinoline

To a stirred solution of 0.30 g (0.00113 moles) of 6-bromo-2-dimethylamino-4-methylquinoline in 30 ml of dry (freshly distilled from over $LiAlH_4$) THF under $N_2$ at −78° C., 1.45 ml (0.00226 moles) of 1.56M n-BuLi was added dropwise over a 5 minute period. 0.23 ml (0.00297 moles) of dry DMF (freshly distilled from over $CaH_2$) was added to the reaction mixture in one portion. The dry ice/acetone bath was removed 12 minutes after the addition of DMF and the solution allowed to warm to −40°. The reaction mixture was poured onto 17 ml of 1N HCl in ice (22 minutes after addition of DMF) and extracted with 30 ml ether. The aqueous solution was made alkaline to pH 12 and extracted with three 20 ml portions of $CH_2Cl_2$. The yellow-orange coloured extract was washed with $H_2O$ and then dried over $MgSO_4$. The solvent was removed under vacuum, and the residue dried in a vacuum oven, wt 0.23 g (95.8%), m.p. 96°–99° C. The product was recrystallised three times (EtOH/$H_2O$). The TLC of the recrystallised product showed several spots, with the predominant component having an $R_f$ 0.38 in 2:1 hexane/EtOAc and being fluorescent under long hot UV. The product was dissolved in 2:1 hexane/EtOAc and placed on silica flash column. Fractions were collected; those containing the $R_f$ 0.38 product were combined, and the solvent removed in vacuo. The residue was recrystallised from absolute ethanol; weight 0.04 g, (17%) m.p. 116.0°–117.8° C. Anal. Calcd. for $C_{13}H_{14}N_2O$: C, 72.87; H, 6.59; N, 13.07. Found: C, 72.74; H, 6.64; N, 13.05.

F. 2,4-Diamino-5-(2-dimethylamino-4-methyl-6-quinolinylmethyl)-pyrimidine

To a solution of 0.5116 g (0.00253 mole) of 2-dimethylamino-6-formyl-4-methylquinoline and 0.3703 g 0.00253 moles) of 3-anilinopropionitrile in 12 ml dry DMSO was added 0.1450 g (0.00268 moles) of CH$_3$ONa in one portion. The temperature of the reaction mixture was then increased to 90° C. and maintained for 2½ hours. The hot brown-red solution was poured onto 50 g ice to give a tan emulsion. The solvent was removed under vacuum and the residue partitioned between 100 ml water and three 20 ml portions of CHCl$_3$. The CHCl$_3$ extract was washed with H$_2$O and evaporated to dryness in vacuo. The residue was taken up in absolute ethanol and filtered through a fritted glass funnel. The filtrate was refrigerated overnight, yielding 0.91 g of solid product, which was again taken up in absolute ethanol and run through a silica pad to remove dark insoluble materials. The filtrate was concentrated under vacuum to leave a brown residue which was dried in a vacuum oven, wt 0.86 g (94.5% m.p. 172°–180° C. A TLC using 2:1 hexane/EtOAc as eluent showed the presence of two minor brightly fluorescent, spots with R$_f$'s 0.51 and 0.38 and two major spots of R$_f$'s 0.28 and 0.11. This product was not further purified but was used directly in the preparation of the pyrimidine.

A solution of free guanidine was prepared by mixing 0.54 g (0.010 moles) of CH$_3$ONa and 0.82 g (0.00858 moles) of guanidine hydrochloride in 20 ml absolute ethanol. The NaCl was removed and resulting guanidine solution was added to a stirred solution of 0.82 g of the anilinopropionitrile adduct in 100 ml of absolute ethanol under N$_2$. The reaction solution was refluxed for 4 hours. Approximately 50 ml of the solvent was then removed under vacuum and the solution cooled in an ice bath. A yellow crystalline product formed; 0.29 g (32.99%). The product was taken up in 45 ml of 20:3 CH$_2$Cl$_2$/CH$_3$OH, placed on silica flash column (15.24 cm), and eluted with 20:3 CH$_2$Cl$_2$/CH$_3$OH. The intense yellow band on the column was collected to give 0.27 g product (30.7%). This product was recrystallised from ethanol, yielding 0.19 g (21.6%), m.p. 218.1°–219.0° C. TLC shows an R$_f$ of 0.14 on silica with 4:1 CH$_2$Cl$_2$/CH$_3$OH.

Anal. Calcd. for C$_{17}$H$_{20}$N$_6$: C, 66.21; H, 6.54; N, 27.25 Found: C, 66.00; H, 6.57; N, 27.21.

EXAMPLE 25

2,4-Diamino-5-(2-methoxy-4-methyl-7-quinolylmethyl)pyrimidine

A. N-(3-Bromophenyl)-3-oxobutyramide

To a heated (80° C., oil bath temperature) solution of 20.00 g (0.12M) of m-bromoaniline in 200 mL of dry toluene was added dropwise over a period of 30 min. 12 g (0.14M) of diketene in 100 mL of dry toluene. When the addition was completed, the reaction mixture was brought to reflux for 5 h. The toluene was then removed in vacuo, resulting in a yellow solid. Recrystallisation from toluene afforded 14.70 g (48%) of product as light pink crystals: mp 94°–95° C.

Anal. Calcd. for C$_{10}$H$_{10}$NO$_2$Br: C, 46.90; H, 3.94; N, 5.47; Br, 31.20. Found: C, 47.02; H, 3.95; N, 5.44; Br, 31.11.

B. 2-Hydroxy-4-methyl-7-bromoquinoline 6.65 g (26.00 mM) of N-(3-bromophenyl)-3-oxobutyramide was heated in 30 mL of conc. sulfuric acid to 120° C. (oil bath temperature) for 1.5 h. The reaction mixture was then poured into ice, whereby precipitate was formed. This was filtered and washed repeatedly with water. After drying, it was recrystallised in 95% ethanol, providing 5.21 g (84%) of the product as a white solid: mp 275°–276° C.;

Anal. Calcd. for C$_{10}$H$_8$NOBr: C, 50.45; H, 3.37; N, 5.88; Br, 33.56. Found: C, 50.46; H, 3.39; N, 5.84; Br, 33.56.

C. 2-Chloro-4-methyl-7-bromoquinoline 5.00 g of 2-hydroxy-4-methyl-7-bromoquinoline was refluxed in 50 mL of phosphorus oxychloride for 2 h. The reaction mixture was then poured into a mixture of ice and conc. ammonium hydroxide. The precipitate resulted from this treatment was filtered and then washed repeatedly with water. It was then taken up in 95% ethanol and heated. Undissolved impurities were filtered, and the filtrate was allowed to crystallise. 3.82 g (71) of the product was obtained as white crystals: mp 73°–74° C.

Anal. Calcd. for C$_{10}$H$_7$NBrCl: C, 46.82; H, 2.75; N, 5.46. Found: C, 46.85; H, 2.79; N, 5.42.

D. 2-Methoxy-4-methyl-7-bromoquinoline

A mixture of 3.00 g (12.00 mM) of 2-chloro-4-methyl-7-bromoquinoline and 0.63 g (12.00 mM) of sodium methoxide was heated to reflux in 30 mL of dry methanol for 48 h. The methanol was then removed in vacuo, and the resultant concentrate was taken up in methylene chloride. This methylene chloride solution was washed repeatedly with saturated sodium chloride. After drying (MgSO$_4$), solvent removal, and recrystallisation from toluene, 2.63 g (87%) of the product was obtained as white crystals: mp 58°–60° C.

Anal. Calcd. for C$_{11}$H$_{10}$NOBr: C, 52.40; H, 4.00; N, 5.56; Br, 31.70. Found: C, 52.25; H, 4.00; N, 5.51; Br, 31.59.

E. 2-Methoxy-4-methyl-7-quinoline carbaldehyde

In a 50 mL flame-dried 3-neck round-bottom flask was dissolved under nitrogen atmosphere 1.50 g (5.90 mM) of 2-methoxy-4-methyl-7-bromoquinoline in 20 mL of freshly distilled THF. This THF solution was then cooled to $-76°$ C. (dry ice/acetone), followed by the dropwise addition (via a syringe) of 7.65 mL of n-BuLi (1.56M of n-BuLi in hexane). After stirring for 5 min., 1.26 mL (16.00 mM) of dry N,N-dimethylformamide was added via a syringe. The reaction mixture was then brought to $-20°$ C. Water was slowly added, then 1N HCl. Following ether extraction and recrystallisation from toluene, 0.90 g (76%) of the product was obtained as a white solid: mp 111°–112° C.

Anal. Calcd. for C$_{12}$H$_{11}$NO$_2$: C, 71.62; H, 5.51; N, 6.96. Found: C, 71.48; H, 5.55; N, 6.92.

F. 2-(2-Methoxy-4-methyl-7-quinolylmethyl)-3-anilinoacrylonitrile.

To a stirred mixture of 0.65 g (3.20 mM) of 2-methoxy-4-methyl-7-quinolinecarbaldehyde and 0.52 g (3.50 mM) of anilinopropionitrile in 10 mL of dry dimethyl sulfoxide was added in one portion 0.19 g (3.50 mM) of sodium methoxide. The resultant mixture was then heated to 90°–95° C. (internal temperature) for 2 h., after which the dimethyl sulfoxide was removed in vacuo. Addition of distilled water to the resultant concentrate resulted in a brown precipitate. This was filtered, washed repeatedly with water and air-dried. Recrystallization from absolute ethanol resulted in 0.49 g (46%) of 2-(2-methoxy-4-methyl-7-quinolylmethyl)-3-anilinoacrylonitrile as a light brown solid: mp 170°–172° C.

Anal. Calcd. for C$_{21}$H$_{19}$N$_3$O: C, 76.57; H, 5.81; N, 12.76. Found: C, 76.34; H, 5.83; N, 12.60.

G. 2,4-Diamino-5-(2-methoxy-4-methyl-7-quinolylmethyl)pyrimidine 0.17 g (1.82 mM) of guanidine hydrochloride and 0.13 g (2.44 mM) of sodium methoxide were stirred for 5 min. under a nitrogen atmosphere. The sodium chloride salt formed was then filtered and the filtrate was added to a round-bottom flask containing 0.20 g (0.61 mM) of 2-(2-methoxy-4-methyl-7-quinolylmethyl)-3-anilinoacrylonitrile. This resultant mixture was heated to reflux for overnight. An equimolar amount of guanidine as above (after treatment with sodium methoxide) was further added and the reaction mixture was refluxed for an additional 24 h. The absolute ethanol was then removed in vacuo. To the resultant concentrate was added methanol/water (9:1). Brown precipitate was formed. This was collected and dried. Following two flash column chromatographies (20–26 g of silica gel, 230–400 mesh, methylene chloride:methanol-9:1), 0.045 g (25%) of the product was obtained as an off-white solid: mp 205°–206° C.; NMR (Me$_2$SO-d$_6$) δ7.90 (d, 1H, J≃8.50 Hz), 7.65 (s, 1H), 7.60 (d, 1H, J≃2 Hz), 7.35 (dd, 1H, J≃8.50, 2 Hz), 7.85 (d, 1H, J≃1 Hz), 6.16 (br s, 23H), 5.76 (br s, 2H), 3.92 (s, 3H), 3.79 (s, 2H), 2.57 (d, 3H, J≃1 Hz).

EXAMPLE 26

Tablets

| Ingredient | Amount per tablet (mg) | |
|---|---|---|
| | Single Active Ingredient | Combination |
| 2,4-Diamino-5-(1,2,3,4-tetrahydro-6-quinolylmethyl)-pyrimidine dihydrochloride | 100.0 | 80.0 |
| Sulfamethoxazole | — | 400.0 |
| Lactose | 84.0 | 100.0 |
| Potato starch, dried | 14.3 | 18.0 |
| Magnesium stearate | 0.7 | 1.0 |
| Polyvinylpyrrolidone | 1.0 | 1.0 |

The 2,4-diamino-5-(1,2,3,4-tetrahydro-6-quinolylmethyl)pyrimidine dihydrochloride, lactose and potato starch (and sulfamethoxazole in the combination formulation) are mixed together and then granulated with aqueous polyvinylpyrrolidone. The granules are dried, mixed with the magnesium stearate and then compressed to produce tablets weighing 200 mg each (single active ingredient) or 600 mg each (combination).

EXAMPLE 27

Capsules

| Ingredient | Amount per capsule (mg) | |
|---|---|---|
| | Single Active Ingredient | Combination |
| 2,4-Diamino-5-(3-quinolylmethyl)-pyrimidine | 100.0 | 80.0 |
| Sulfisoxazole | — | 160.0 |
| Lactose | 149.0 | 79.0 |
| Corn starch | 149.0 | 79.0 |
| Stearic acid | 2.0 | 2.0 |

The ingredients are thoroughly mixed and then loaded into hard gelatin capsules containing 400 mg each.

EXAMPLE 28

Ampoules

| Ingredient | Amount per ampoule |
|---|---|
| 2,4-Diamino-5-(1,2,3,4-tetrahydro-4-methyl-6-quinolylmethyl)pyrimidine dihydrochloride | 5.0 mg |
| Water for injection, q.s. to | 1.0 ml |

The 2,4-diamino-5-(1,2,3,4-tetrahydro-4-methyl-6-quinolylmethyl)pyrimidine dihydrochloride is dissolved in the water and the solution sterilized by ultrafiltration. The sterile solution is delivered into sterile capsules and the ampoules sealed, the entire operation being carried out under sterile conditions.

EXAMPLE 29

2,4-Diamino-5-(1,2-dihydro-2,2,4-trimethyl-6(1H)quinolylmethyl)pyrimidine.dihydrochloride 1,2-Dihydro-2,2,4-trimethylquinoline (1.73 g, 10 mmol) was treated by the method of Example 1 with 2,4-diamino-5-hydroxymethylpyrimidine and worked up in the same manner. The crude product was purified on a silica gel column eluting with methylene chloride:methanol/19:1, followed by recrystallization in ethanol with 2 equivalents of hydrochloric acid to give the title compound; mp 260°–264°. Anal. Calcd. for C$_{17}$H$_{21}$N$_5$.2HCl.0.5H$_2$O: C, 54.12; H, 6.41; N, 18.56. Found: C, 54.48; H, 6.51; N, 18.17.

We claim:

1. A compound which is selected from 2,4-diamino-5-(1,2,3,4-tetrahydro-6-quinolylmethyl)pyrimidine, 2,4-diamino-5-(1,2,3,4-tetrahydro-8-(2-methoxyethoxy)-6-quinolylmethyl)pyrimidine, and 2,4-diamino-5-(1,2,3,4-tetrahydro-4-methyl-6-quinolylmethyl)pyrimidine or a pharmaceutically acceptable salt thereof.
2. 2,4-diamino-5-(1,2,3,4-tetrahydro-6-quinolylmethyl)pyrimidine dihydrochloride.
3. 2,4-diamino-5-(1,2,3,4-tetrahydro-4-methyl-6-quinolylmethyl)-pyrimidine-dihydrochloride.

* * * * *